(12) United States Patent
Sereno et al.

(10) Patent No.: US 9,629,697 B2
(45) Date of Patent: Apr. 25, 2017

(54) PROSTHODONTIC DEVICE

(71) Applicant: INVIBIO LIMITED, Lancashire (GB)

(72) Inventors: Nuno Sereno, Merseyside (GB);
Marcus Jarman-Smith, Lancashire (GB)

(73) Assignee: INVIBIO LIMITED, Lancashire (GB)

( * ) Notice: Subject to any disclaimer, the term of this patent is extended or adjusted under 35 U.S.C. 154(b) by 466 days.

(21) Appl. No.: 14/360,685

(22) PCT Filed: Nov. 22, 2012

(86) PCT No.: PCT/GB2012/052895
§ 371 (c)(1),
(2) Date: May 27, 2014

(87) PCT Pub. No.: WO2013/076493
PCT Pub. Date: May 30, 2013

(65) Prior Publication Data
US 2014/0343707 A1 Nov. 20, 2014

(30) Foreign Application Priority Data

Nov. 25, 2011 (GB) .................................. 1120375.9

(51) Int. Cl.
*G06F 19/00* (2011.01)
*A61C 13/00* (2006.01)
(Continued)

(52) U.S. Cl.
CPC ...... *A61C 13/0004* (2013.01); *A61C 13/0022* (2013.01); *A61K 6/087* (2013.01);
(Continued)

(58) Field of Classification Search
CPC . A61C 13/0004; A61C 13/0022; A61C 13/34; A61C 13/0006; A61C 13/10; A61C 13/0001; A61C 13/0013; A61C 13/102; A61C 13/225; A61C 7/002; A61C 7/08; A61C 8/00; A61C 7/00; C08L 71/00; C08L 33/10; G06F 17/50; Y10T 29/49567;
(Continued)

(56) References Cited

U.S. PATENT DOCUMENTS 7,758,346 B1 * 7/2010 Letcher ................ A61C 8/0048
433/172
7,806,691 B2 * 10/2010 Berger ................. A61C 13/275
433/167
(Continued)

OTHER PUBLICATIONS

Thierry Copponnex, "High performance polymer PEKK: the material of the future," Cendres +Metaux SA, Mar. 2011, XP002692681, Retrieved from the Internet <URL: http://www.cmsa.ch/SiteCollectionDocuments/Brochure_Pekkton_EN_Web.pdf>.
(Continued)

*Primary Examiner* — Darrin Dunn
(74) *Attorney, Agent, or Firm* — Michael Best & Friedrich LLP

(57) ABSTRACT

A framework for a removable, partial or complete prosthodontic device is made by machining, using a CAD/CAM technique, a disc 2, made from polyetheretherketone, to define the framework 4. Prosthetic teeth and gums can be secured to the framework to define the prosthodontic device.

11 Claims, 13 Drawing Sheets

(51) Int. Cl.
    *A61K 6/087* (2006.01)
    *G05B 19/18* (2006.01)
    *A61C 13/01* (2006.01)
(52) U.S. Cl.
    CPC ............ *G05B 19/182* (2013.01); *A61C 13/01* (2013.01); *G05B 2219/2647* (2013.01)
(58) Field of Classification Search
    CPC .... Y10T 409/303752; Y10T 29/49568; A61K 6/083; A61K 6/09; A61K 6/0017; G05B 19/4097; G05B 2219/45167
    See application file for complete search history.

(56) References Cited

U.S. PATENT DOCUMENTS

| | | | | |
|---|---|---|---|---|
| 8,352,060 B2* | 1/2013 | Chun | ................. | A61C 11/00 700/118 |
| 8,509,932 B2* | 8/2013 | Kopelman | ............ | A61C 8/0001 434/172 |
| 8,738,340 B2* | 5/2014 | Dunne | ................. | A61B 5/4547 433/25 |
| 8,751,031 B2* | 6/2014 | Sager | ................. | A61C 5/10 700/96 |
| 9,439,739 B2* | 9/2016 | Jana | ................. | A61C 13/0006 |
| 2004/0241614 A1 | 12/2004 | Goldberg et al. | | |
| 2004/0245664 A1* | 12/2004 | Panzera | ................. | A61K 6/024 264/16 |
| 2005/0019121 A1* | 1/2005 | Suttor | ................. | A61C 13/0004 409/131 |
| 2005/0260377 A1* | 11/2005 | Bramer | ................. | A61C 13/0022 428/67 |
| 2006/0008774 A1* | 1/2006 | Orth | ................. | A61C 13/0022 433/202.1 |
| 2006/0040236 A1* | 2/2006 | Schmitt | ................. | A61C 13/0004 433/213 |
| 2007/0056467 A1* | 3/2007 | Panzera | ................. | A61K 6/024 106/35 |
| 2007/0190488 A1* | 8/2007 | Rusler | ................. | A61C 13/0025 433/171 |
| 2007/0298655 A1 | 12/2007 | Auderset et al. | | |
| 2008/0153069 A1* | 6/2008 | Holzner | ................. | A61C 13/20 433/223 |
| 2008/0234532 A1* | 9/2008 | De Langen | ............ | A61B 90/39 600/8 |
| 2008/0254402 A1* | 10/2008 | Hilliard | ................. | A61C 7/08 433/24 |
| 2009/0053677 A1* | 2/2009 | Orth | ................. | A61C 13/0004 433/215 |
| 2009/0098511 A1 | 4/2009 | Zhang | | |
| 2009/0220917 A1 | 9/2009 | Jensen | | |
| 2009/0274994 A1* | 11/2009 | Jung | ................. | A61C 13/0022 433/202.1 |
| 2009/0287332 A1* | 11/2009 | Adusumilli | ........ | A61C 13/0004 700/98 |
| 2009/0291417 A1* | 11/2009 | Rubbert | ................. | A61C 7/00 433/215 |
| 2010/0035209 A1* | 2/2010 | Jang | ................. | A61C 13/273 433/194 |
| 2010/0076114 A1* | 3/2010 | Devine | ................. | A61L 27/18 523/113 |
| 2010/0152873 A1* | 6/2010 | Dunne | ................. | A61B 5/4547 700/98 |
| 2010/0167238 A1* | 7/2010 | Kopelman | ......... | A61C 13/0004 433/172 |
| 2010/0279254 A1* | 11/2010 | White | ................. | A61C 13/00 433/213 |
| 2011/0020761 A1* | 1/2011 | Kalili | ................. | A61C 7/08 433/6 |
| 2011/0049738 A1* | 3/2011 | Sun | ................. | A61K 6/09 264/16 |
| 2011/0151259 A1* | 6/2011 | Jarman-Smith | .......... | C08J 3/203 428/402 |
| 2011/0196524 A1* | 8/2011 | Giasson | ............. | A61C 13/0004 700/103 |
| 2011/0212420 A1* | 9/2011 | Vuillemot | .......... | A61C 13/0004 433/215 |
| 2011/0275031 A1* | 11/2011 | Jana | ................. | A61C 13/0006 433/172 |
| 2011/0276159 A1* | 11/2011 | Chun | ................. | A61C 13/0004 700/98 |
| 2012/0065952 A1* | 3/2012 | Kopelman | ......... | A61C 13/0004 703/11 |
| 2012/0179281 A1* | 7/2012 | Steingart | ............ | A61C 13/0004 700/97 |
| 2012/0214133 A1* | 8/2012 | Jung | ................. | A61C 8/005 433/174 |
| 2012/0322025 A1* | 12/2012 | Ozawa | ................. | A61C 9/0053 433/29 |
| 2013/0004919 A1* | 1/2013 | Kirchner | ................. | A61C 8/005 433/174 |
| 2013/0172441 A1* | 7/2013 | Takahata | ................. | A61C 13/0022 523/115 |
| 2013/0203009 A1* | 8/2013 | Mutsafi | ................. | A61C 8/0001 433/27 |
| 2013/0218531 A1* | 8/2013 | Deichmann | ............ | A61C 9/004 703/1 |
| 2013/0218532 A1* | 8/2013 | Thompson | .............. | G06T 17/00 703/1 |
| 2013/0316302 A1* | 11/2013 | Fisker | ................. | A61C 13/0004 433/171 |
| 2014/0051037 A1* | 2/2014 | Fisker | ................. | A61C 8/0048 433/213 |
| 2015/0037760 A1* | 2/2015 | Thompson | ......... | A61C 13/0004 433/214 |
| 2015/0134094 A1* | 5/2015 | Thompson | ......... | A61C 13/0004 700/98 |
| 2016/0008108 A1* | 1/2016 | Thompson | ......... | A61C 13/0004 433/213 |
| 2017/0014212 A1* | 1/2017 | Fischer | ................. | A61C 13/081 |
| 2017/0020639 A1* | 1/2017 | Jahns | ................. | A61C 8/0012 |

OTHER PUBLICATIONS

Invibio, "Invibio PEEK-OPTIMA polymer provides platform for Dentanium's new non-metallic and non ceramic material," Press releases, Mar. 16, 2007, XP002692680, U.K., Retrieved from the Internet <URL:http://www.invibio.com/press-room/releases-preview.php?id=60>.
International Search Report and Written Opinion for Application No. PCT/GB2012/052895 dated Mar. 12, 2013 (10 pages).

* cited by examiner

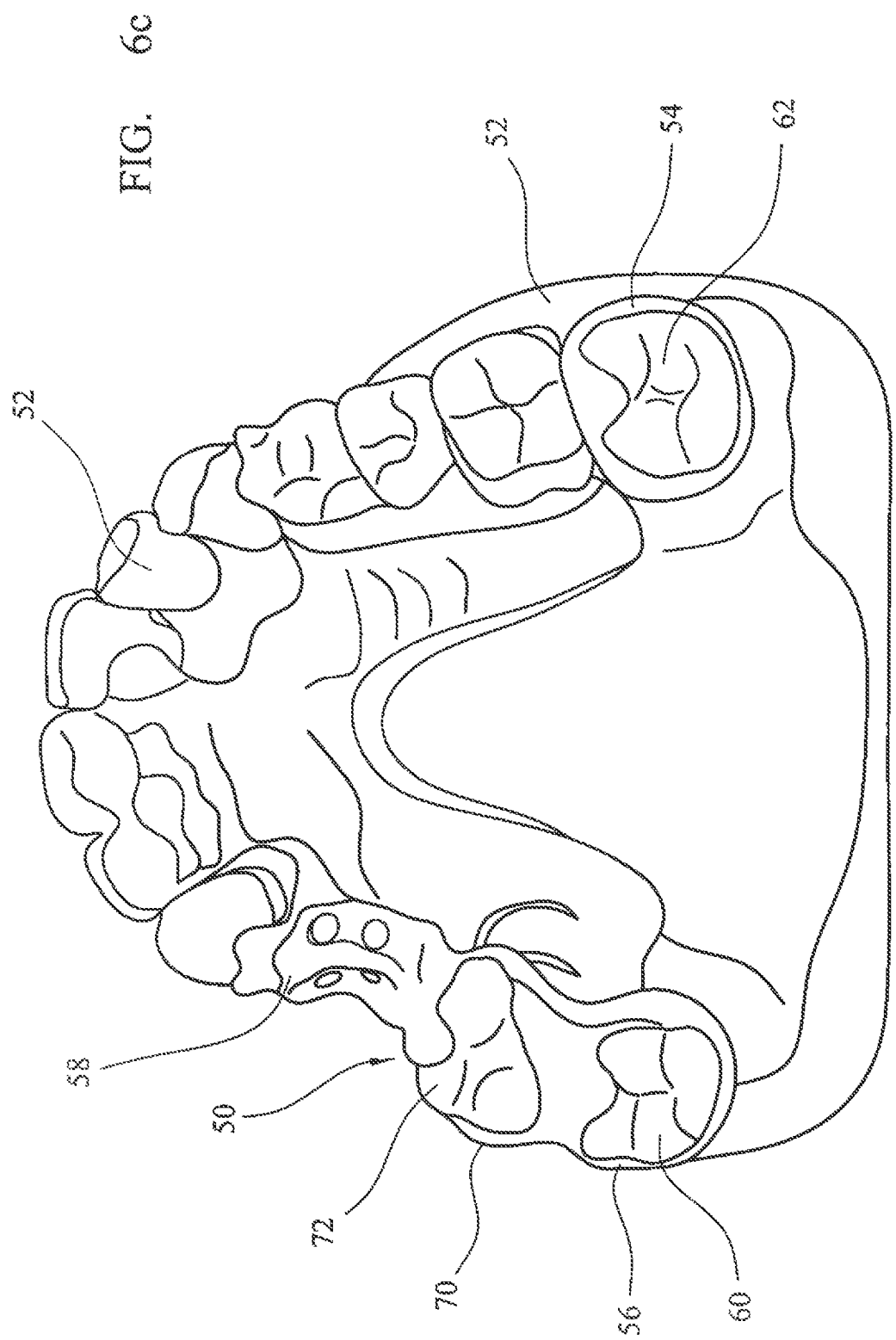

PROSTHODONTIC DEVICE

This invention relates to a prosthodontic device, parts thereof, a method of making such a device and blanks for use in the method.

Prosthodontics relates, inter alia, to treatments to address missing or deficient teeth in patients. One type of prosthodontic device is fixed within patients' mouths, for example by screws or adhesive and therefore is not removable by patients under normal conditions. Such prosthodontic devices may comprise crowns, bridges, implants or abutments. A second type of prosthodontic device is arranged to replace patients' missing teeth and contiguous tissue with a prosthesis which is designed to be removed by a wearer, for example nightly. Such removable prostheses may comprise removable partial prosthodontic devices which cooperate with patients' natural remaining teeth (or implants) to define a complete dentition; or may comprise complete prosthodontic devices which define the entire patients' dentition.

There are many different types of prosthodontic devices and methods of making such devices. For example, removable prosthodontic devices often comprise a metal framework (e.g. of cobalt chrome) in combination with cast or moulded plastics parts. However, disadvantageously, such devices may be heavy, difficult to manufacture to produce an accurate mouth-fit, and have high stiffness and poor load distribution, leading to patient discomfort. Additionally, use of metal may result in relatively high levels of metal ions being introduced into patients' bodies over time. Furthermore, some patients are allergic to metals used in the devices. In addition, manufacture of existing prosthodontic devices, especially those which include a combination of metal and plastics, can be time-consuming; and such devices may be aesthetically poor One type of denture in which metal is extensively used to define a framework which locks to at least two of a patient's existing teeth (or to at least two implants) is known as a precision attachment denture. The framework is very accurately made from metal which has the disadvantages referred to. In addition, since metal has little elasticity, it is held in position on a tooth (or implant) largely by friction, rather than "gripping" the tooth (implant), to any extent. Also, it may be time-consuming for a dentist or technician to adjust the framework to optimise its fit.

A second type of denture is referred to as a telescopic denture. Again, in this case, an accurately manufactured metal framework is made which is arranged to engage at least two of a patient's existing teeth (or at least two implants). The challenges and disadvantages are similar to those for the precision attachment denture.

A third type of denture is referred to as an implant supported denture or implant retained denture. In this case, an accurately manufactured metal framework is made which is arranged to engage at least four implants. The challenges and disadvantages are similar to those for the precision attachment denture.

Perhaps the greatest ongoing challenge associated with prosthodontic devices is to improve patients' experience in use by providing devices which are comfortable, fit well and function well when chewing. It is an object of the present invention to address the problems.

In general terms, it is an object of the present invention to address problems associated with prosthodontic devices.

It is an object of preferred embodiments of the invention to address problems associated with the second type of prosthodontic devices described—i.e. removable prosthodontic devices.

It is an object of preferred embodiments of the invention to address problems associated with precision attachment dentures and/or telescopic dentures and/or implant supported dentures.

According to a first aspect of the invention, there is provided a method of making a prosthodontic device which includes the steps of:

(i) selecting a blank from which a framework for the device can be machined, wherein said blank comprises a polymeric material which comprises a repeat unit of formula (I)

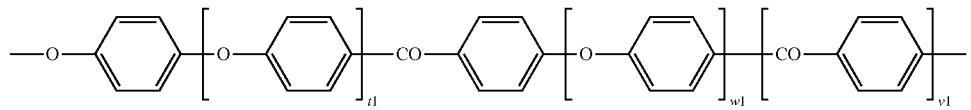

where t1 and w1 independently represent 0 or 1 and v1 represents 0, 1 or 2;

(ii) using digital technology to collate data to define the shape and dimensions of the framework;

(iii) machining the blank in dependence upon the data.

Advantageously, the method can be used to make a framework and a prosthodontic (especially a removable prosthodontic) device which improves a patient's experience, since a flexible framework can be accurately made, with a minimum amount of materials which have a high strength-weight ratio, excellent load transfer (e.g. when chewing) and improved flexibility and/or elasticity which facilitates mouth retention.

The framework may be made with regions of different roughness, for example Ra. Preferably, the roughness (eg Ra) of first areas of the framework which directly contact parts of a patient's mouth in use have lower roughness compared to second areas of the framework to which prosthetic teeth and/or gums are secured. The ratio of the roughness of a said second area to a said first area is suitably at least 2, at least 5 or at least 8. The ratio may be less than 50. Areas of different roughness may be formed when the blank is machined in step (iii) or the roughness may be adjusted by one or more separate treatments (e.g. polishing and/or grit-blasting) after step (iii).

The blank selected in step (i) suitably has a thickness of at least 10 mm, suitably at least 15 mm. The thickness may be less than 60 mm. The blank preferably has a substantially constant thickness in one direction. The blank preferably has a main face which has an area in the range 4000 mm² to 8000 mm². The blank may have a maximum diameter of at least 75 mm, preferably in the range 75-100 mm.

Said blank is preferably disc-shaped. It preferably has a main face which is symmetrical about two orthogonal planes and, especially, has a substantially constant circular cross-section along its extent.

Said polymeric material preferably consists essentially of a repeat unit of formula I. Preferred polymeric materials comprise (especially consist essentially of) a said repeat unit wherein t1=1, v1=0 and w1=0; t1=0, v1=0 and w1=0; t1=0, w1=1, v1=2; or t1=0, v1=1 and w1=0. More preferred comprise (especially consist essentially of) a said repeat unit wherein t1=1, v1=0 and w1=0; or t1=0, v1=0 and w1=0. The most preferred comprises (especially consists essentially of) a said repeat unit wherein t1=1, v1=0 and w1=0.

In preferred embodiments, said polymeric material is selected from polyetheretherketone, polyetherketone, polyetherketoneetherketoneketone and polyetherketoneketone. In a more preferred embodiment, said polymeric material is selected from polyetherketone and polyetheretherketone. In an especially preferred embodiment, said polymeric material is polyetheretherketone.

Said polymeric material may have a Notched Izod Impact Strength (specimen 80 mm×10 mm×4 mm with a cut 0.25 mm notch (Type A), tested at 23° C., in accordance with ISO180) of at least 4 $KJm^{-2}$, preferably at least 5 $KJm^{-2}$, more preferably at least 6 $KJm^{-2}$. Said Notched Izod Impact Strength, measured as aforesaid, may be less than 10 $KJm^{-2}$, suitably less than 8 $KJm^{-2}$. The Notched Izod Impact Strength, measured as aforesaid, may be at least 3 $KJm^{-2}$, suitably at least 4 $KJm^{-2}$, preferably at least 5 $KJm^{-2}$. Said impact strength may be less than 50 $KJm^{-2}$, suitably less than 30 $KJm^{-2}$.

Said polymeric material suitably has a melt viscosity (MV) of at least 0.06 $kNsm^{-2}$, preferably has a MV of at least 0.09 $kNsm^{-2}$, more preferably at least 0.12 $kNsm^{-2}$, especially at least 0.15 $kNsm^{-2}$. Advantageously, the MV may be at least 0.35 $kNsm^{-2}$ and especially at least 0.40 $kNsm^{-2}$ An MV of 0.45 $kNsm^{-2}$ has been found to be particularly advantageous in the manufacture of accurate, strong frameworks.

MV is suitably measured using capillary rheometry operating at 400° C. at a shear rate of 1000 $s^{-1}$ using a tungsten carbide die, 0.5 mm×3.175 mm.

Said polymeric material may have a MV of less than 1.00 $kNsm^{-2}$, preferably less than 0.5 $kNsm^{-2}$.

Said polymeric material may have a MV in the range 0.09 to 0.5 $kNsm^{-2}$, preferably in the range 0.14 to 0.5 $kNsm^{-2}$, more preferably in the range 0.4 to 0.5 $kNsm^{-2}$.

Said polymeric material may have a tensile strength, measured in accordance with ISO527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

Said polymeric material may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

Said polymeric material may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

Said polymeric material may be amorphous or semi-crystalline. It is preferably crystallisable. It is preferably semi-crystalline.

The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning Calorimetry (DSC).

The level of crystallinity of said polymeric material may be at least 1%, suitably at least 3%, preferably at least 5% and more preferably at least 10%. In especially preferred embodiments, the crystallinity may be greater than 25%. It may be less than 50% or less than 40%. Preferably the prosthodontic device includes a framework having the aforementioned levels of crystallinity.

The main peak of the melting endotherm (Tm) of said polymeric material (if crystalline) may be at least 300° C.

Said blank may be made from a composition which includes said polymeric material described and other components, for example colourants (e.g. pigments, ceramics, metal oxides (eg. titanium dioxide)) or fillers (for example reinforcing or wear enhancing fillers or fibres, bioactive fillers such as bioglasses, soluble glasses, zeolites containing antibacterial agents such as silver ions, nanosilver, ceramics such as HA or substituted HA or treatment agents such as antibiotic doped HA or compounds favourable to the gingiva, diagnostic agents such as radiopaque fillers such as barium sulphate, aesthetic fillers such as reflective agents and light refracting agents, fillers conveying some taste or flavour altering or enhancing effect or breath freshening effect). Said composition may include 0-10 wt %, suitably 0-6 wt % of colourants. Colourants may be selected so the composition is pink or white. Colourants may occur so that the colour is graduated. In one embodiment, the composition includes no colourant. When a filler is included in the composition, it is suitably included to improve the mechanical properties of the composition and/or a framework made from the composition. However, it has been found that frameworks with excellent mechanical properties can be made without addition of any fibrous fillers. When a filler is included it may be selected from glass fibre and carbon fibre. Such a filler may be present at 0-50 wt % based on the weight of the polymeric material.

Preferably, said composition comprises at least 80 wt %, at least 90 wt % or at least 94 wt % of said polymeric material. The balance may comprise one or more colourants.

In step (ii), digital technology is used to collate data on the region into which the prosthodontic device is to fit. Step (ii) preferably includes scanning a region into which the prosthetic device is to fit (e.g. scanning a patient's mouth) or scanning of a model of a region into which the device is to fit. Preferably, data is collated from a model, for example a cast, obtained of a patient's mouth and/or dentition. Step (ii) may comprise use of Computer-aided design (CAD) technology.

The method preferably includes a step prior to step (ii) of taking an impression of a patient's mouth. The impression may be used to collate said data. The method preferably involves a CAD/CAM technique whereby data is collated as aforesaid and computer-aided manufacture (CAM) is undertaken in step (iii). Thus, in step (iii), a computer suitably controls the machining of the blank.

Preferably, the selected blank is positioned in a CAD/CAM machine and the machine is arranged to machine the blank in dependence upon the data.

Preferably, machining of said blank is undertaken using at least 5-axis machining, suitably under computer control. In some cases, higher axis (e.g. 7-axis) machining may be undertaken. Machining in step (iii) suitably comprises milling. The work piece is suitably cooled during machining so as to control crystallinity of the machined blank.

Preferably, after step (iii), a framework is produced which includes no metal and preferably consists essentially of material derived from said blank.

Using the method, a framework of great accuracy can be made which can be fitted in position in a patient's mouth with no need for alteration. The method may be particularly advantageously used to produce a framework for a precision attachment denture or a telescopic denture. In both of these cases, the framework suitably includes at least two female elements which are arranged to engage male elements (which may comprise a patient's natural teeth or implants and/or parts secured to such natural teeth or implants). The female elements preferably comprise sockets which are arranged to receive the aforementioned male elements. Walls which define the sockets suitably include regions of thickness less than 2 mm, less than 1.5 mm or even 1 mm or less. The method allows such female elements to be accurately defined, in terms of cross-sectional shape and depth and accurately positioned relative to each other so the framework is substantially a perfect fit upon the male elements and does not require adjustment, as is often required when metal frameworks are used. Furthermore, the material which defines the sockets is resilient and/or has some elasticity so the sockets can be flexed slightly upon engagement with the male elements; and when correctly positioned upon the male elements any slight flexing can relax leading to the sockets gripping the male elements to a small extent which facilitates retention of the framework (and thereby the prosthodontic device) in a patient's mouth.

Said framework made in the method preferably includes an area of thickness less than 2 mm. Said framework preferably includes an area of at least 0.5 cm², preferably at least 1 cm² which has a thickness of less than 2 mm.

Said framework preferably includes an area of thickness less than 1.5 mm. Said framework preferably includes an area of at least 0.2 cm², preferably at least 1 cm² which has a thickness of less than 1.5 mm. Said framework preferably includes an area of less than 1.0 mm. Said framework preferably includes an area of at least 0.5 cm², preferably at least 1 cm² which has a thickness of less than 1.0 mm.

Advantageously, machining can be used to produce a framework which is mechanically advantageous compared to frameworks made by injection moulding or made of metal.

Preferably, the framework includes openings, for example holes which extend through the framework. The holes preferably have an area of less than 10 mm², or less than 8 mm² or less than 6 mm². The holes may have an area of at least 1 mm². The framework suitably includes at least 4, preferably at least 6, more preferably at least 8 holes. Preferably, holes are positioned in regions of said framework which are to be covered with prosthetic teeth and/or gum-like material, suitably to facilitate keying of the prosthetic teeth and/or gum-like material on the framework.

The method preferably includes the step of securing (preferably permanently securing) prosthetic teeth to the framework. Prior to the securing step, the method may include roughening an area of the framework to which prosthetic teeth and/or gums are to be attached. Prosthetic teeth and/or gums may be formed by standard techniques but are suitably applied over said holes which extend through the framework. For example, prosthetic gum material may be applied over the holes and it may penetrate the holes to facilitate keying of the material to the framework. The prosthetic teeth are suitably secured in position by adhesive means. The teeth may be made from acrylic or other plastics material.

Said prosthodontic device suitably includes less than 2 wt % of metal, preferably less than 1 wt % of metal, more preferably less than 0.5 wt % of metal, especially less than 0.1 wt % of metal. Said device is preferably substantially metal-free.

Said prosthodontic device is preferably the second type of device as described in the introduction of the present specification. It is preferably a removable prosthodontic device, i.e. removable by a patient in normal use. It may be a removable partial prosthodontic device; or may be a removable complete prosthodontic device. Advantageously, it may be a precision attachment denture or a telescopic denture.

According to the second aspect of the invention, there is provided a prosthodontic device made in the method of the first aspect per se.

The device may have any feature of the device described according to the first aspect.

According to a third aspect, there is provided a framework for a prosthodontic device, said framework being machined, wherein said framework comprises a polymeric material which comprises a repeat unit of formula (I)

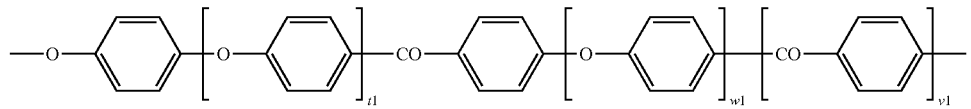

where t1 and w1 independently represent 0 or 1 and v1 represents 0, 1 or 2.

Said machined framework preferably includes identifiable machining marks

Said framework may have any feature of the framework of the first aspect.

According to a fourth aspect, there is provided a prosthodontic device comprising a framework according to the third aspect to which is secured a plurality of teeth prostheses which are arranged to mimic natural teeth Said teeth prostheses may be secured to the framework by adhesive means and or by penetration of part of the prostheses into openings in the framework.

Said device may include gum prostheses arranged to mimic natural gum

According to a fifth aspect of the invention, there is provided a blank for use in the method of the first aspect, said blank consisting essentially of a composition which includes a polymeric material and other components, for example colourants (e.g. pigments) or fillers (for example fibrous fillers), wherein said polymeric material comprises a repeat unit of formula (I)

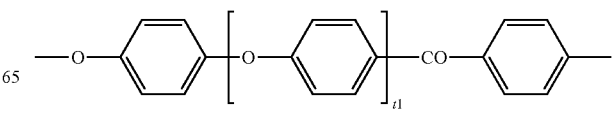

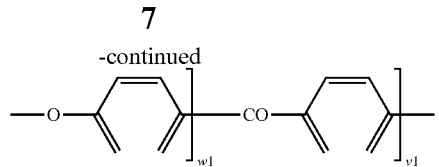

where t1 and w1 independently represent 0 or 1 and v1 represents 0, 1 or 2.

Said blank, said composition and said polymeric material may have any features described in the other aspects According to a sixth aspect of the invention, there is provided a method of making a blank for use in the method of the first aspect, the method comprising:
(i) selecting a composition;
(ii) extruding the composition to define an extruded part, for example rod;
(iii) forming discs from the part, for example by cutting the part perpendicular to the elongate axis of the extrudate.

The invention of the first aspect may include a step prior to step (i) which comprises making a blank as described according to the sixth aspect.

Any invention described herein may be combined with any feature of any other aspect of any other invention or embodiment described herein mutatis mutandis.

Specific embodiments of the invention will now be described, by way of example, with reference to the accompanying figures in which:

FIG. 6c is a plan view of the device/model of FIGS. 6a and 6b;

The following material is referred to hereinafter:
PEEK-OPTIMA (Trade Mark) LT1—polyetheretherketones (PEEK) of melt viscosity (MV) of 0.45 kNsm$^{-2}$.

Figure 1:
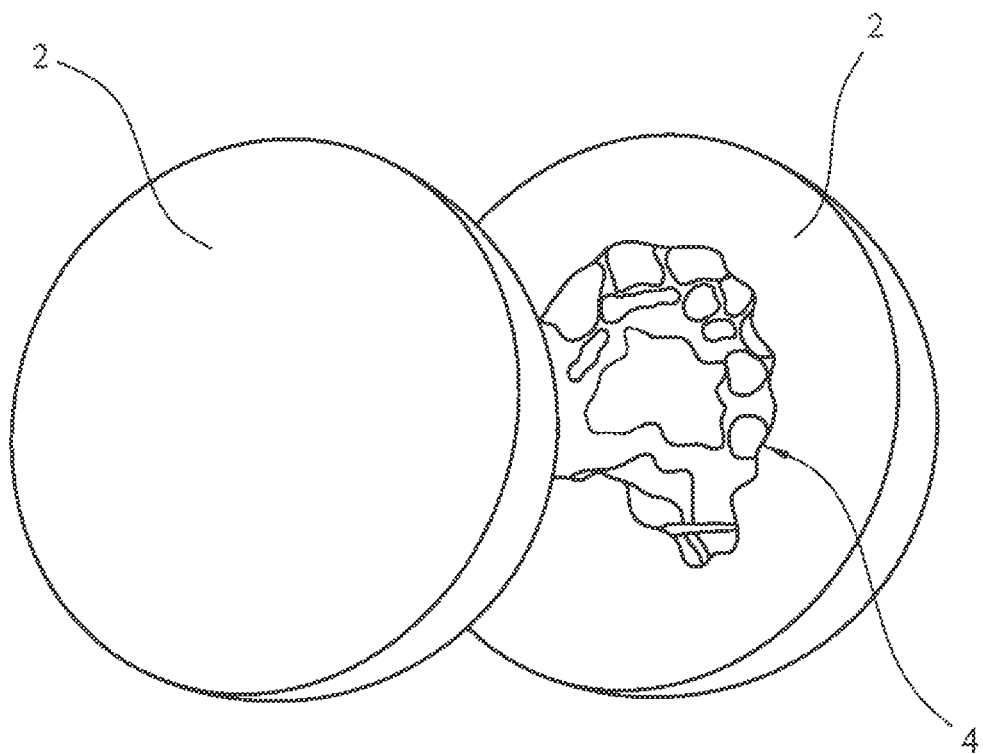
FIG. 1 is a front view of one blank before machining and one blank after machining.
Figure 3:
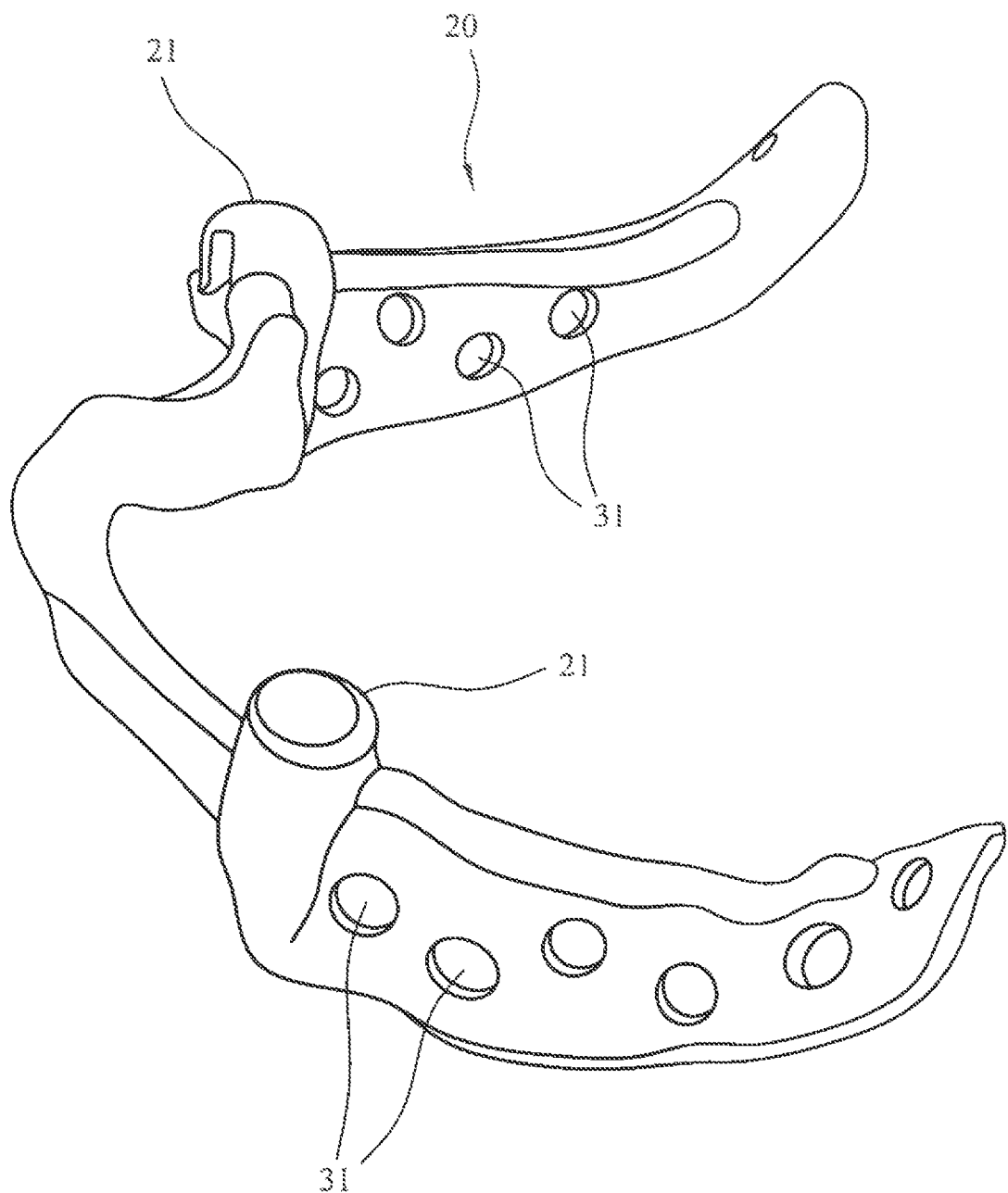
FIG. 3 is a perspective view of a removable framework of a precision attachment denture which is a partial prosthodontic device.
Figure 4:
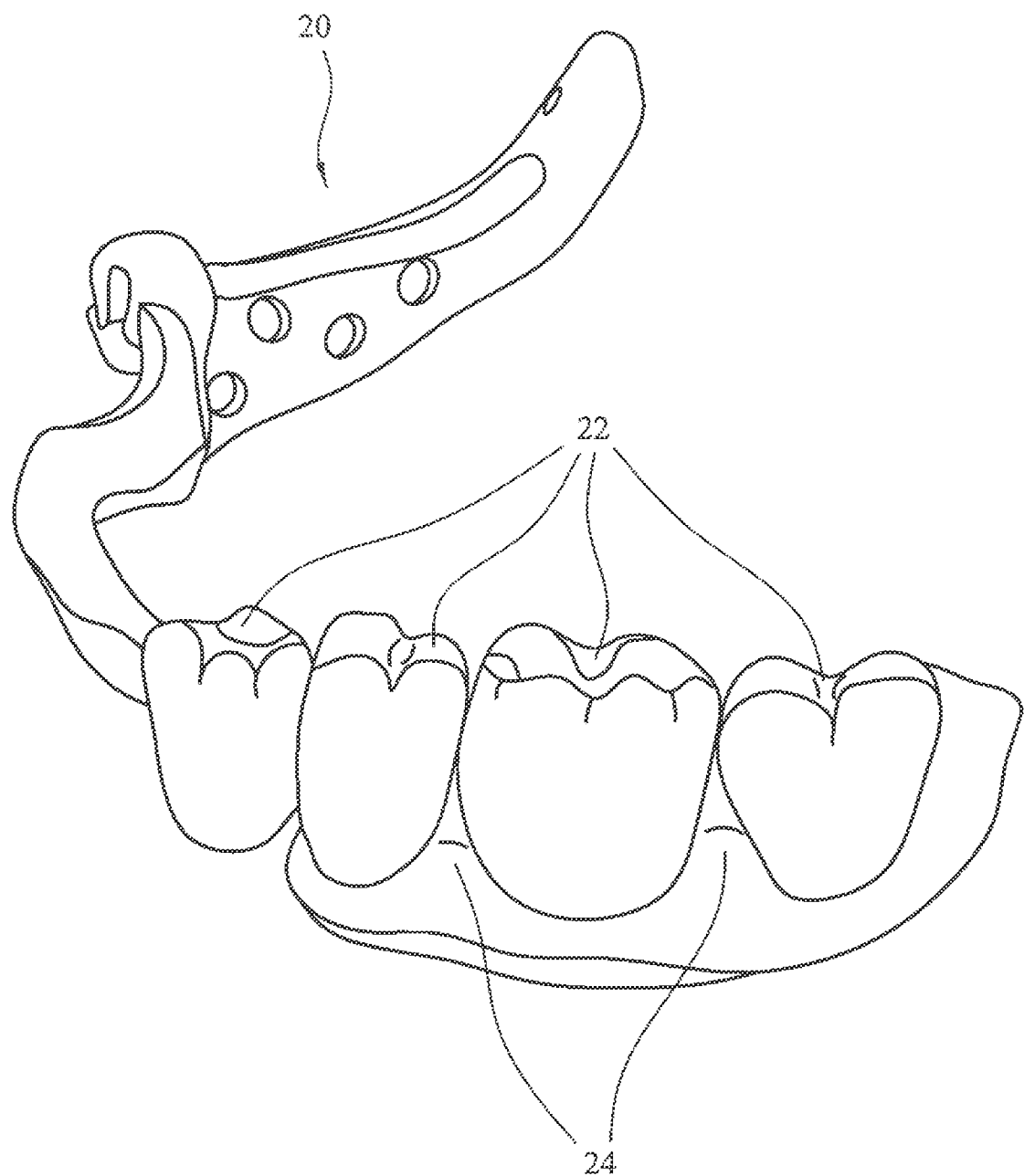
FIG. 4 shows the framework of FIG. 3 with prosthetic teeth attached on one side only.
Figure 5:
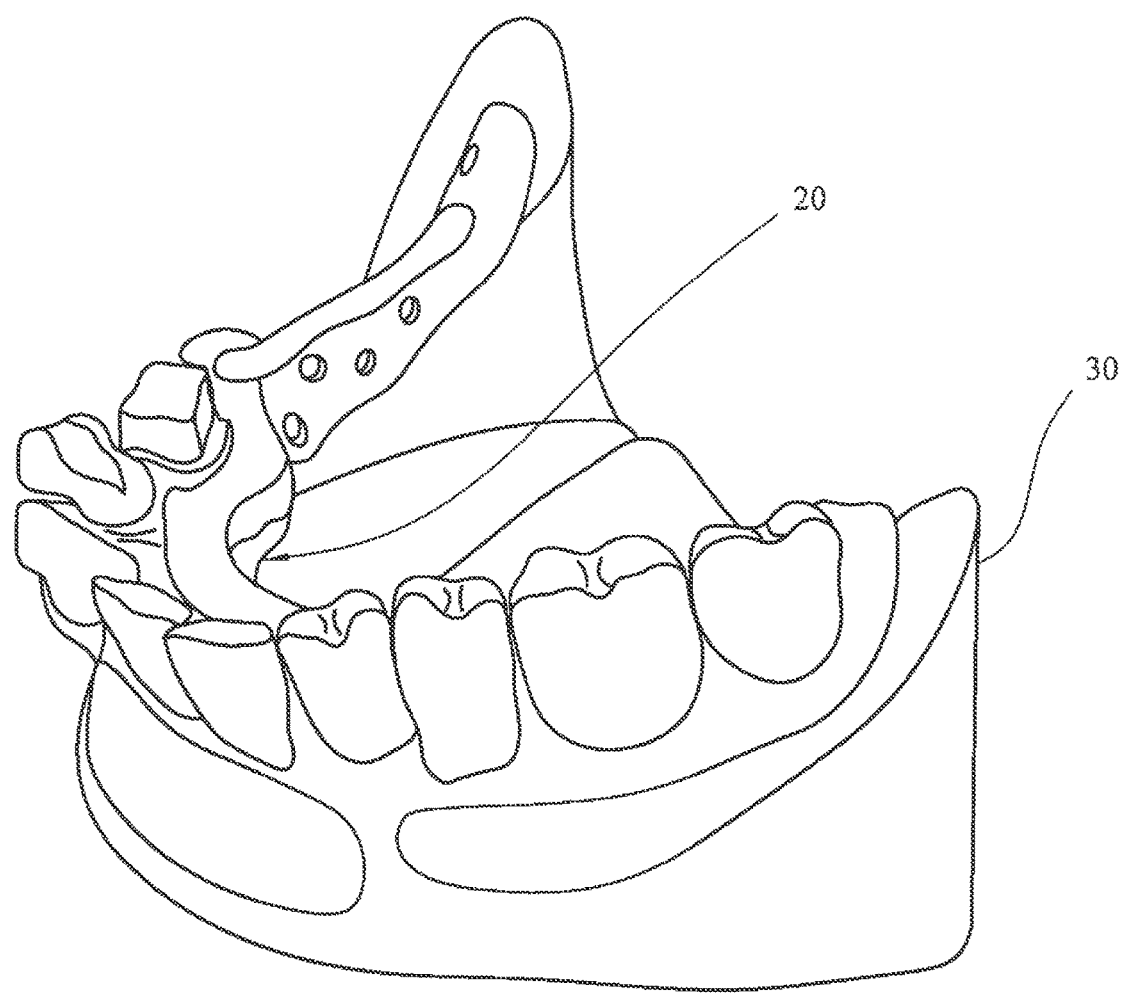
FIG. 5 shows the device of FIG. 4 in position on a model.

A framework for a removable partial or complete prosthodontic device, for example as illustrated in FIGS. 4 to 6, is made by machining, using a CAD/CAM technique, a disc 2, made from polyetheretherketone PEEK OPTIMA LT1 shown in FIG. 1 to define the framework 4 (FIGS. 1 and 3). Prosthetic teeth and gums can then be secured to the framework to define the prosthodontic device.

Further details on the device and parts thereof are provided below.

EXAMPLE 1—MANUFACTURE OF PEEK DISCS

Granules of PEEK OPTIMA LT1 were extruded to produce rods of constant diameter, suitably in the range 75 mm-100 mm, and subsequently the rod was machined to form discs of constant thickness, suitably in the range 10-30 mm.

EXAMPLE 2—MANUFACTURE OF CUSTOMIZED FRAMEWORK FOR PROSTHODONTIC DEVICE

The following steps are undertaken:
(i) Moulds are taken of a patient's mouth using standard impression trays. The moulds are then poured with dental plaster and allowed to set.
(ii) A mould is scanned to collate relevant CAD data which is input into a 5-axis CAD-CAM machine. An operator then designs the framework and device in conjunction with the machine. The machine is suitably set up to prepare a CAD design for the manufacture of the framework (CAM) from a PEEK disc made in Example 1.
(iii) A PEEK disc 2 (FIG. 1) is inserted in the CAD/CAM machine which operates automatically to machine a customized framework 4 (FIG. 1) from the disc, based on data collated from scanning the mould.
(iv) The framework is removed from the disc and finished to define a framework which can be fitted accurately into a patient's mouth after prosthetic teeth and gums have been constructed upon it. Areas of the framework which are to contact parts of a patient's mouth may be polished so they are smooth; whereas areas of the framework which are to carry prosthetic teeth and gums may be roughened by shot blasting or the like. In some cases, the CAD-CAM machine may be set up to define areas of different roughness—e.g. to define very smooth areas which are to contact parts of a patient's mouth and rougher areas which are to carry prosthetic teeth and gums.

Figure 2A:
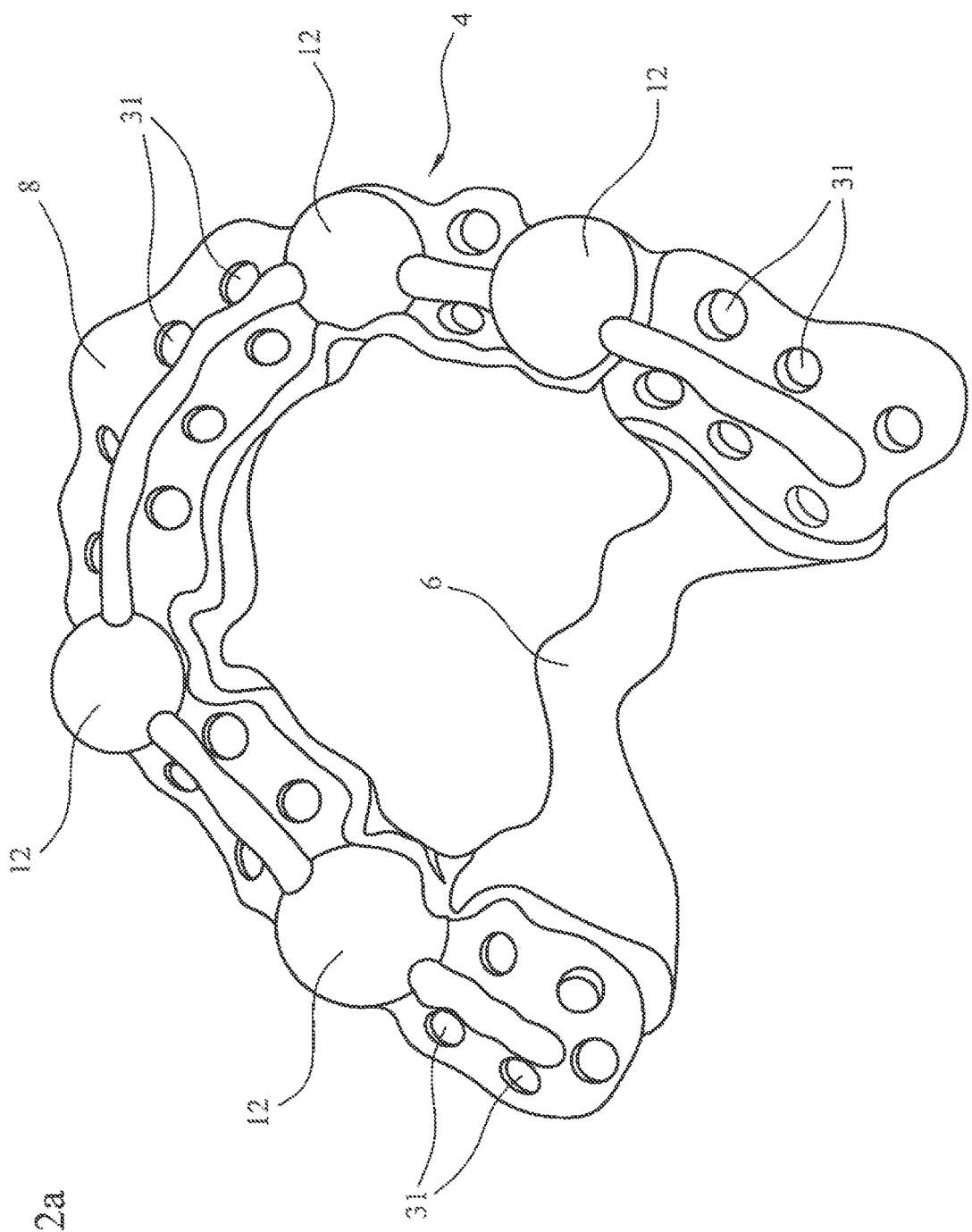
FIG. 2a is a perspective view of a face of a complete removable framework for a telescopic prosthodontic device which face is arranged to carry prosthetic teeth.
Figure 2B:
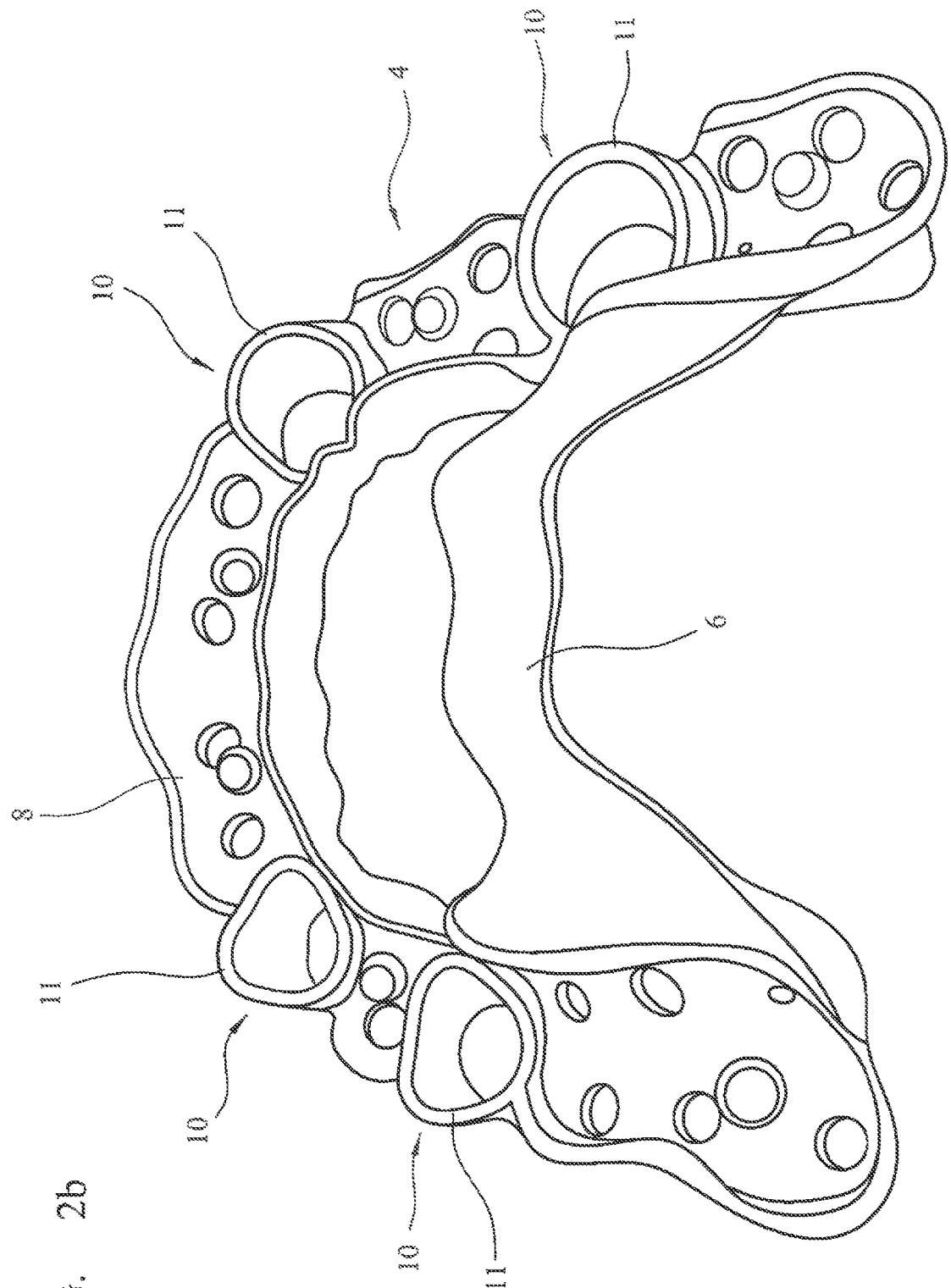
FIG. 2b is a view of the device of FIG. 2a showing an opposite face of the device which engages a crown or implant and/or the gums of a patient in use.

FIG. 2 provides an example of a framework 4 made using the method of Example 2, for a telescopic denture device. Such a device is time-consuming to prepare by prior techniques since it must be made with great accuracy. The framework includes a central portion 6 which is arranged to rest against the roof of a patient's mouth and a curved support 8 which is arranged to carry prosthetic teeth and gums. In the example shown, the framework 4 includes four spaced apart sockets 10 (FIG. 2b) which appears as bulbous domes 12 in the FIG. 2a view. The sockets may be arranged to engage male elements which may be remnants of a patient's natural teeth (or implants); or more likely engage parts secured to a patient's natural teeth or implants. The framework must be very accurately prepared for it to be a comfortable fit on the male elements. The manufacturing method is able to achieve such a fit without any need for manual correction. The walls 11 which define the sockets 10 may be 1 mm thick or less and the PEEK material used has resilience and elasticity. As a result, the framework may be designed so the walls of the sockets flex outwardly very slightly on engagement of the sockets with the male elements. The walls then relax when the framework is seated in its correct position. Thus, the sockets may slightly grip the male elements in use, facilitating retention of the framework (and the device which incorporates the framework) in the patient's mouth.

FIG. 3 provides an example of a framework 20 which may be made as described for the FIG. 2 framework. The framework 20 may be for a precision attachment denture which like the telescopic denture described with reference to FIG. 2 requires very accurate manufacture of the framework. Referring to FIG. 3, the framework 20 includes female elements 21 in the form of sockets which are arranged to accurately releasably engage male elements defined by a patient's natural teeth or implants or more likely engage parts secured to a patient's natural teeth or implants. The framework is secured to at least two male elements and is able to accurately resiliently engage the male elements as described above with reference to FIG. 2.

EXAMPLE 3—MANUFACTURE OF PROSTHODONTIC DEVICE

It should be noted from FIGS. 2a, 2b and 3 that the frameworks include many openings 31 extending from one side of the framework to the opposite side. These openings are positioned in areas of the framework which are to be overlaid with prosthetic teeth and/or gums.

Prosthetic teeth and gums may be built up by standard techniques in a layering process. A first material, which may be pink, is laid down over the opening 31. The material may be resinous and/or fluid so it may flow into the openings thereby securing the first material by keying into the framework. Subsequent layers and/or teeth prostheses may be built up over the first layer. It is found that the process described can be used to securely engage the prosthetic teeth/gums to the framework.

FIG. 4 shows prosthetic teeth 22 and pink gums 24 formed on one side of the framework 20 and FIG. 5 shows the framework 20 engaged with a dental plaster mould 30.

Figure 6A:
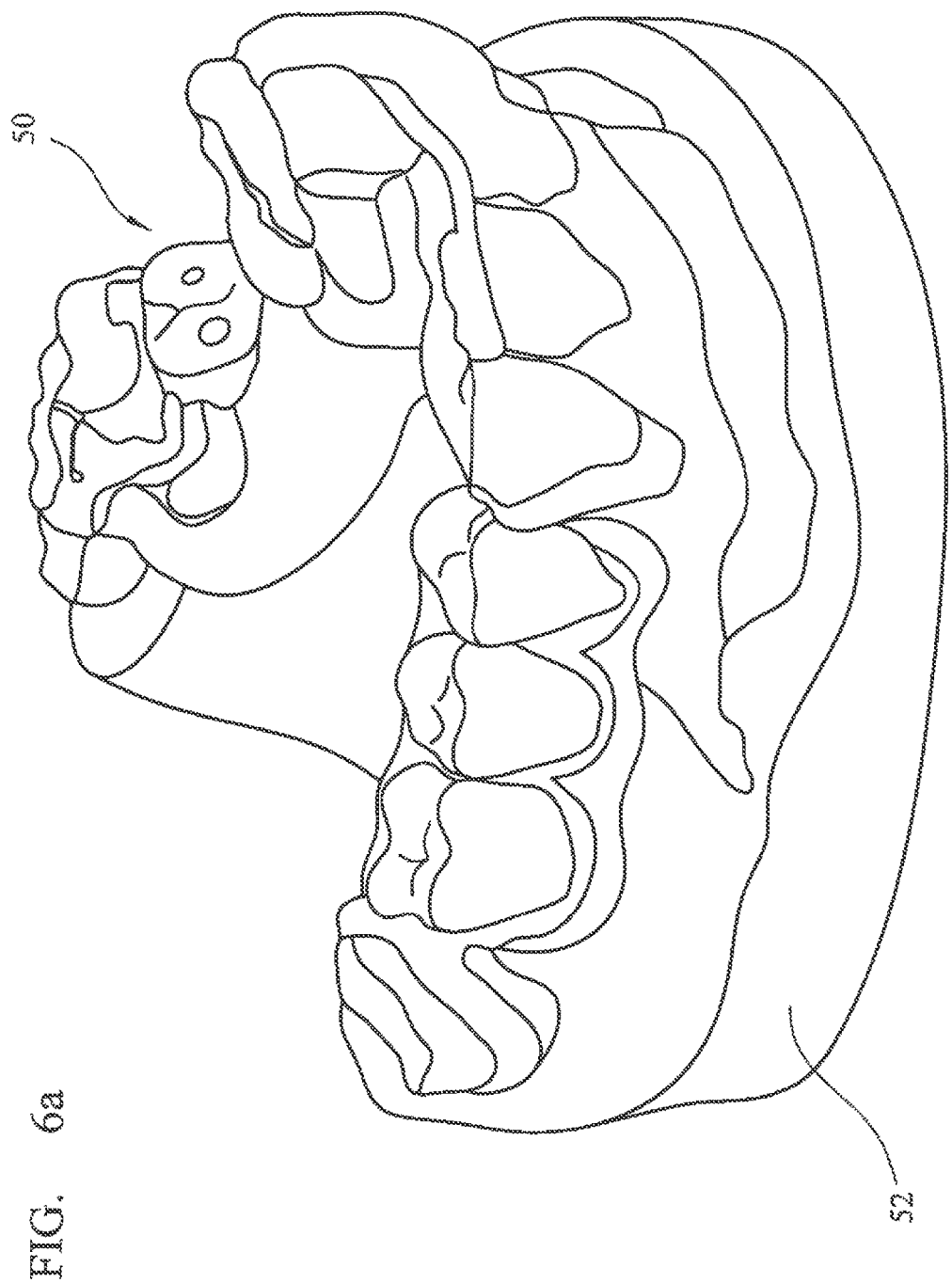
FIG. 6a shows a removable partial prosthodontic device on a model, the device incorporating denture clasps which engage natural teeth.
Figure 6B:
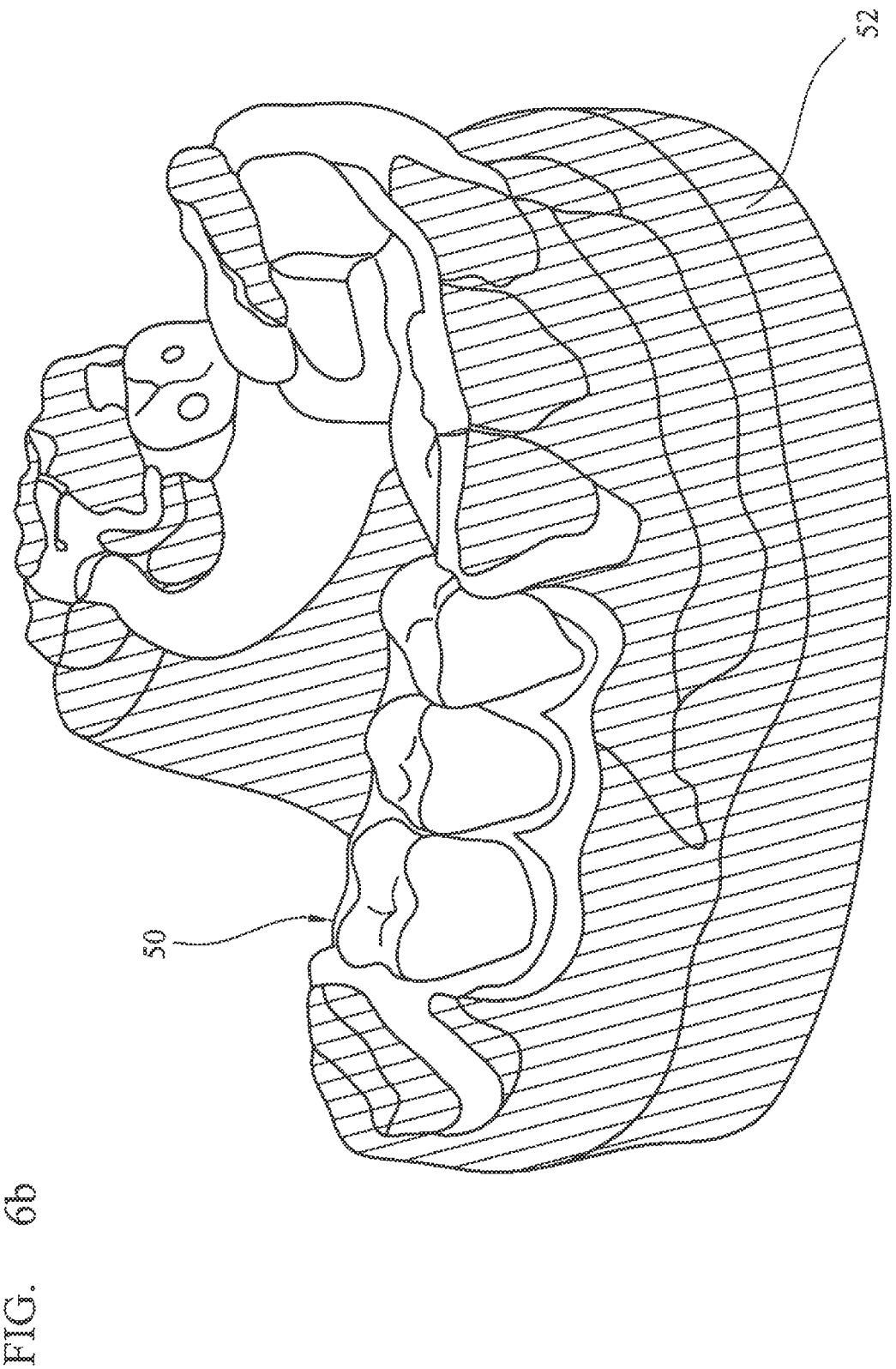
FIG. 6b is the view of FIG. 6a showing the model in hatched lines to highlight the complexity of the device.
Figure 6D:
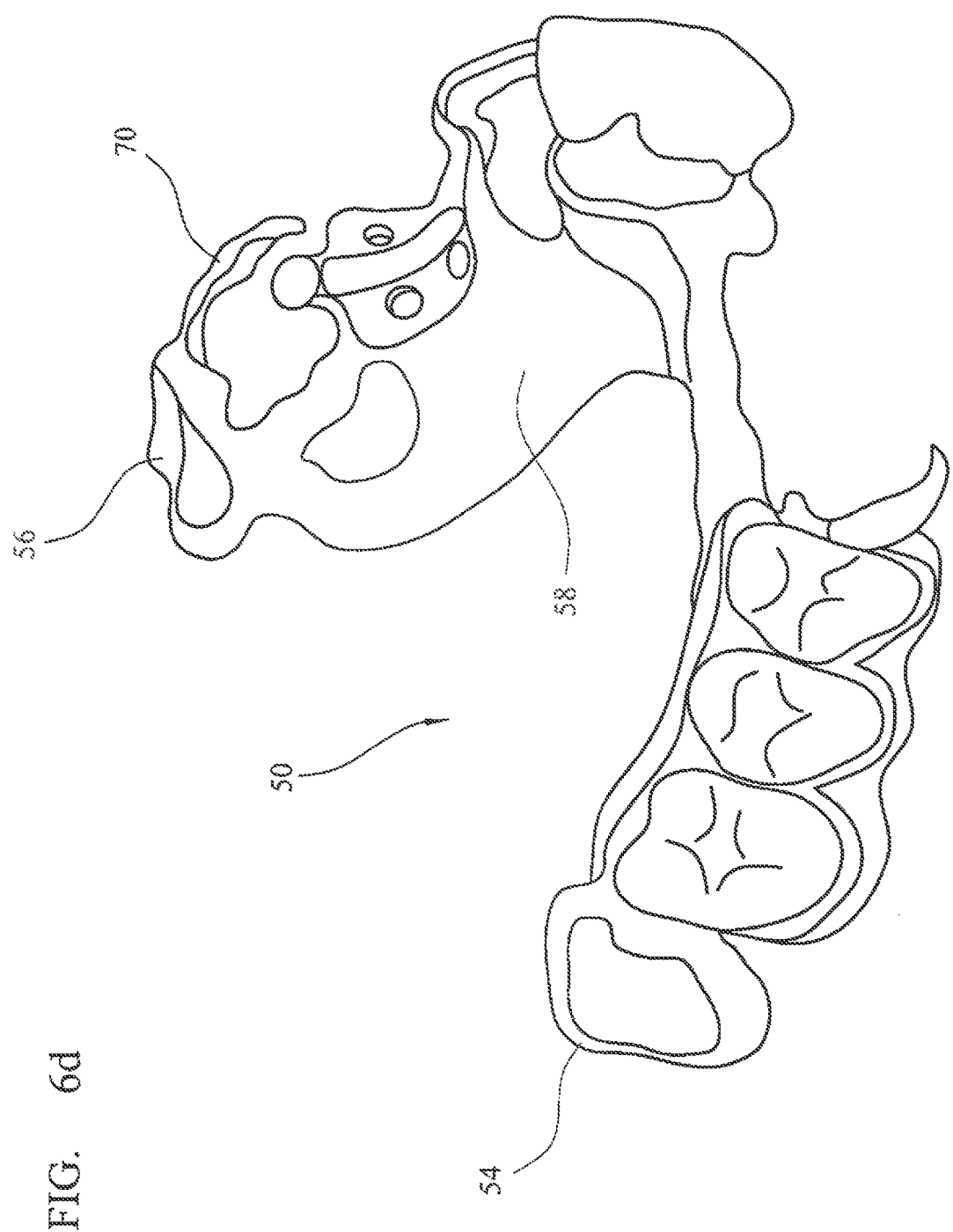
FIG. 6d shows the device of FIGS. 6a-6c removed from the model.

PEEK may be used in the methods described to produce highly complex frameworks and prosthodontic devices as illustrated in FIGS. 6a-6d. FIG. 6d shows a prosthodontic device 50 removed from a mould 52, whereas FIGS. 6a-6c shown it upon the mould 52. The 6b figure includes a cross hatched mould to highlight the complex arrangement of the device 50.

Referring to FIG. 6, the device 50 includes clasps 54, 56 at outer ends of framework 58. The clasps define fully enclosed openings which releasably engage two remaining teeth (defined as teeth 60, 62 on the mould). The clasps are defined by PEEK and have a thickness of 1 mm or less. In addition, a resilient hook arrangement 70 is defined inwards of clasp 56 and is arranged to hook around molar tooth 72. Other intricate features of the device 50 will be apparent from the figures. It is as a result of the material used and use of machining as described which enables such complex shapes to be produced for a prosthodontic device which has high mechanical strength, fatigue resistance and a long life-expectancy.

Blanks hereinafter described may be made to improve efficiencies and reduce wastage that may otherwise arise during milling to define prosthodontic devices using CAD-CAM technology. A blank is suitably provided which is inclusive of a required bridge size.

Figure 7:
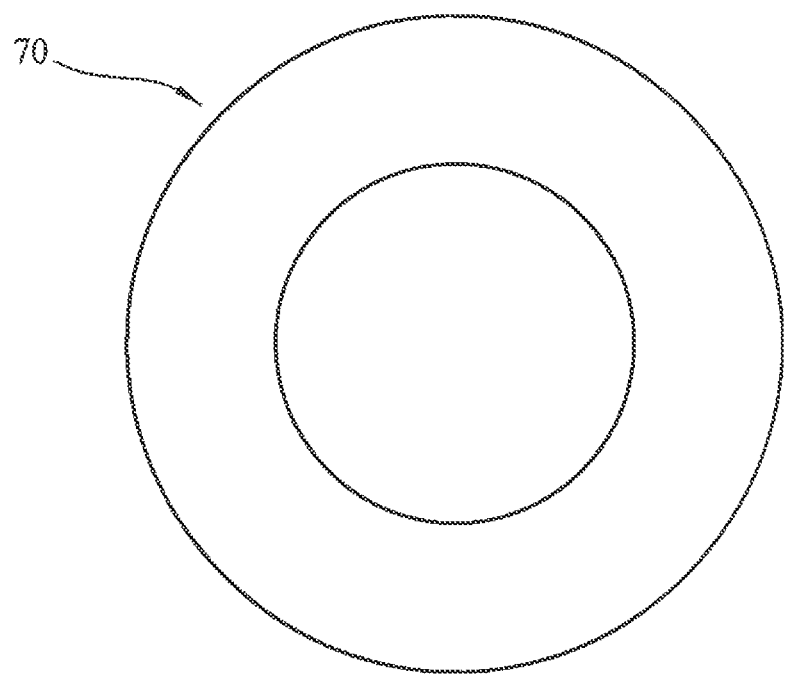
FIGS. 7 to 11 are front views of respective alternative blanks.
Figure 8:
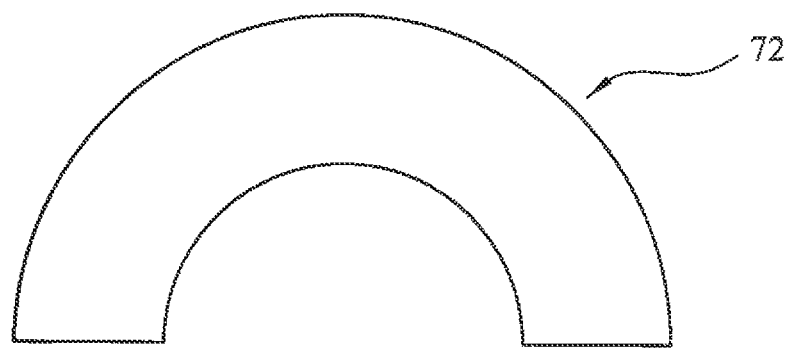
Figure 9:
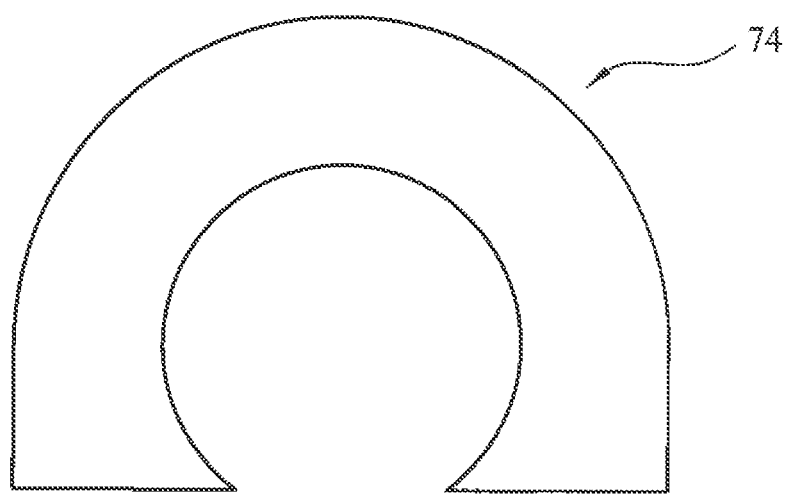
Figure 10:
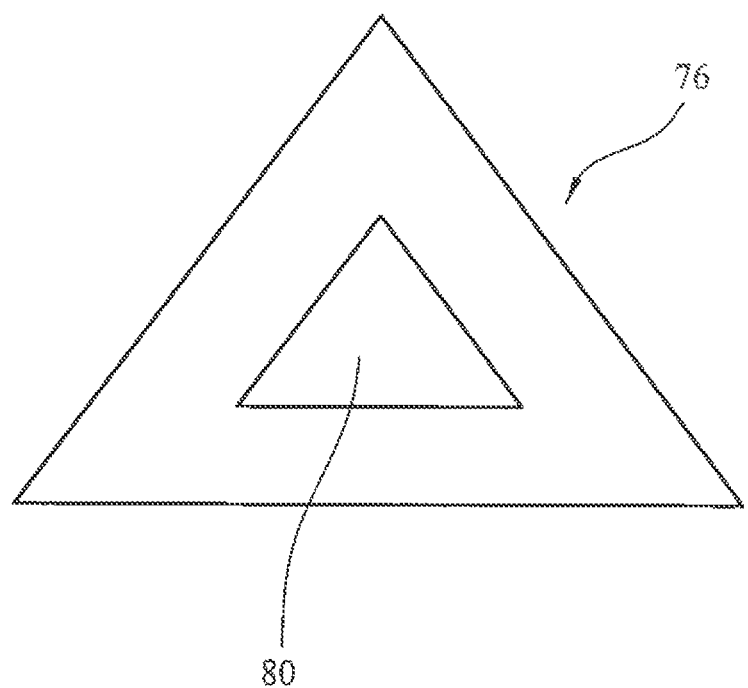
Figure 11:
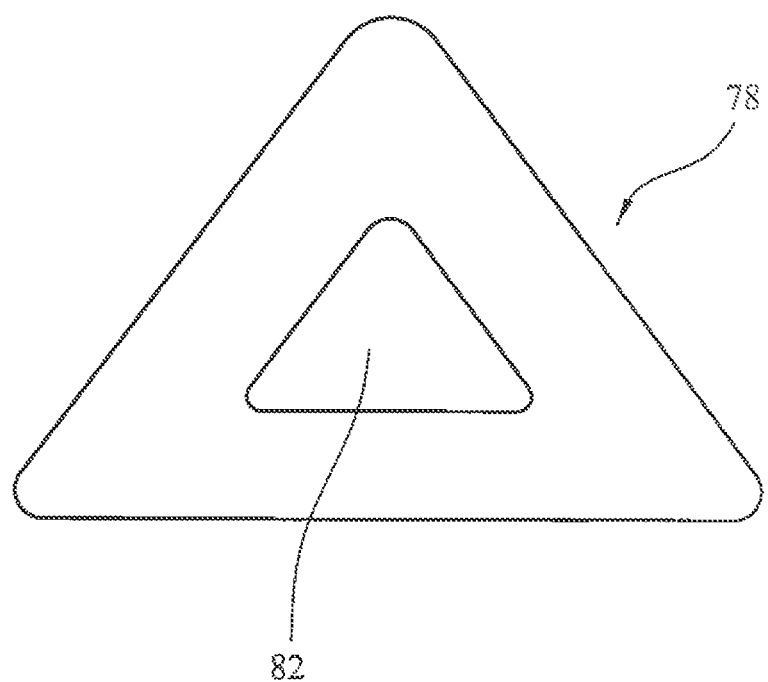

Referring to FIG. 7, an annular cross-section blank 70 may be advantageous over the blank of FIG. 1 by virtue of using a reduced amount of material. As an alternative one annular blank may be formed into two semi-annular blanks, one 72 of which is shown in FIG. 8. Such a blank may advantageously be used for certain prosthodontic devices. Blank 74 is a further alternative shape which uses a reduced amount of material compared to the blank of FIG. 1. Further alternative blanks 76 and 78 shown in FIGS. 10 and 11 are triangular with respective triangular openings 80, 82 being defined.

The blanks of FIGS. 7 to 11 may advantageously be made by extrusion using a suitable die arranged to define the cross-sections shown. The extruded part may then be cut transversely to define discs having the cross-sections shown. The blank 72 of FIG. 8 may be formed by machining from the annular extrusion of FIG. 7.

As an alternative to use of extrusion as described, the blanks described may be made by injection or compression moulding. Alternatively, the blanks may be made by laser sintering or other rapid prototyping techniques such as 3D printing.

The blanks described herein may be made from pink-coloured polyetheretherketone which is as close to natural gum colour as possible. The selection of such a material may reduce labour, time and cost involved in preparing prosthodontic devices by reducing the need to use an opaque material and reducing the amount of veneer required and the work necessary to produce a gum-like region in the final device.

Pink-coloured polyetheretherketone may be preferable to metals for transversal connector sections in telescopic dentures.

The use of PEEK in the method described may have advantages as follows:
 frameworks of high mechanical strength and fatigue resistance can be produced;
 the frameworks are flexible, and have excellent strength to weight ratio, thereby increasing patient comfort;
 the frameworks have improved load distribution while retaining strength;
 the frameworks can be machined with greater accuracy than can be achieved by injection moulding of plastics (wherein shrinkage in the mould can be problematic) or by use of metal frameworks) enabling them to be advantageously used for telescopic dentures and precision attachment dentures;
 the frameworks produce a good soft tissue response and stimulate bone;
 the frameworks have improved friction in use, which aids retention in position in a patient's mouth;
 the frameworks have a neutral taste, are heat resistant, highly chemically resistant and non-corrosive;
 the frameworks are more aesthetically acceptable compared to metal frameworks.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of making a prosthodontic device which includes the steps of:
 (i) selecting, a blank from which a framework for the device can be machined, wherein said blank comprises a polymeric material which comprises a repeat unit of formula (I)

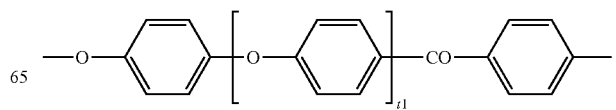

-continued

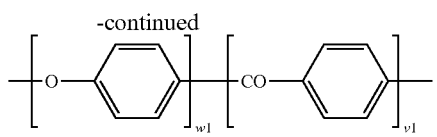

where t1 and w1 independently represent 0 or 1 and v1 represents 0, 1 or 2;
(ii) using digital technology to collate data to define shape and dimensions of the framework;
(iii) machining the blank in dependence upon the data;
wherein said polymeric material comprises a repeat unit wherein t1=1, v1=0, and w1=0;
said blank is made from a composition which comprises at least 90 wt (weigh) % of said polymeric material;
machining of said blank is undertaken using at least 5-axis machining;
said framework includes at least two female elements which are arranged to engage male elements, said female elements comprising sockets which are arranged to receive the male elements and wherein walls which define the sockets include regions of thickness less than 1 mm; and
said framework includes an area of at least 1 cm² which has a thickness of less than 15 mm; the framework includes at least 4 holes Which extend through the framework and have an area of less than 10 mm².

2. The method according to claim 1, wherein said framework is made with regions of different roughness.

3. The method according to claim 1, wherein the roughness of first areas of the framework which directly contact parts of a patient's mouth in use is lower compared to second areas of the framework to which prosthetic teeth and/or gums are secured.

4. The method according to claim 1, wherein said blank selected in step (i) has a thickness of at least 10 mm and a thickness of less than 60 mm; a main face which has an area in the range 4000 mm² to 8000 mm²; a maximum diameter of at least 75 mm; and a main face which is symmetrical about two orthogonal planes.

5. The method according to claim 1, wherein in step (ii), digital technology is used to collate data on the region into which the prosthodontic device is to fit.

6. The method according to claim 1, wherein after step (iii), a framework is produced which includes no metal and consists essentially of material derived from said blank.

7. The method according to claim 1, which is used to produce a framework for a precision attachment denture or telescopic denture.

8. The method according to claim 1, wherein said framework includes an area of at least 0.5 cm² which has a thickness of less than 2 mm.

9. The method according to claim 1 which includes the step of securing prosthetic teeth to the framework.

10. The method according to claim 1, wherein said prosthodontic device includes less than 2 wt % of metal.

11. The method according to claim 1, which is a removable prosthodontic device.

* * * * *

UNITED STATES PATENT AND TRADEMARK OFFICE
CERTIFICATE OF CORRECTION

| | |
|---|---|
| PATENT NO. | : 9,629,697 B2 |
| APPLICATION NO. | : 14/360685 |
| DATED | : April 25, 2017 |
| INVENTOR(S) | : Nuno Sereno et al. |

It is certified that error appears in the above-identified patent and that said Letters Patent is hereby corrected as shown below:

In the Claims

In Claim 1, on Column 11, Line 26:
Please delete "15 mm" and insert --1.5 mm--.

Signed and Sealed this
Third Day of October, 2017

Joseph Matal
*Performing the Functions and Duties of the*
*Under Secretary of Commerce for Intellectual Property and*
*Director of the United States Patent and Trademark Office*